United States Patent [19]

Wood et al.

[11] Patent Number: 5,783,423
[45] Date of Patent: Jul. 21, 1998

[54] YEAST STRAINS

[75] Inventors: Patricia Carolyn Wood, Burton-on-Trent; Alan Victor Quirk, Costock, both of United Kingdom

[73] Assignee: Delta Biotechnology Ltd., United Kingdom

[21] Appl. No.: 750,077

[22] PCT Filed: Jun. 7, 1995

[86] PCT No.: PCT/GB95/01317

§ 371 Date: Feb. 20, 1997

§ 102(e) Date: Feb. 20, 1997

[87] PCT Pub. No.: WO95/33833

PCT Pub. Date: Dec. 14, 1995

[30] Foreign Application Priority Data

Jun. 7, 1994 [GB] United Kingdom ............ 9411356

[51] Int. Cl.⁶ .......... C12P 21/02; C12N 1/19; C07K 1/14

[52] U.S. Cl. .......... 435/69.6; 435/254.11; 435/254.2; 435/254.21; 435/254.22; 435/254.23; 435/256.8; 435/320.1; 530/344; 530/350; 530/363; 530/364

[58] Field of Search .......... 435/69.1, 69.6, 435/69.7, 172.1, 172.3, 320.1, 254.1, 254.11, 254.2, 254.22, 254.21, 254.23, 256.8; 530/350, 344, 362, 363, 364

[56] References Cited

PUBLICATIONS

Mol Gen Genet, vol. 239, pp. 273–280, 1993.
Bio/Technology, vol. 8, pp. 42–46, 1990.

*Primary Examiner*—David Guzo
*Attorney, Agent, or Firm*—Irving Newman; Naomi S. Biswas

[57] ABSTRACT

Reduction (preferably elimination) of the HSP150 protein in a yeast used to produce desired foreign proteins, especially human albumin, facilitates purification of the protein.

29 Claims, 3 Drawing Sheets

5' AND 3' REGIONS OF HSP150 GENE OBTAINED BY PCR

⇩ ⇩

CLONED INTO pUC19    CLONED INTO pUC19

⇩ ⇩

⇩ ⇩

SEQUENCED    SEQUENCED

⇩ ⇩

EcoRI/HindIII FRAGMENT ISOLATED    EcoRI/HindIII FRAGMENT ISOLATED

FIG_1

LIGATE ClaI/SalI URA3 FRAGMENT
INTO ClaI/XhoI CUT pAYE505

YEAST STRAINS

1. Field of the Invention

The present invention relates to the production of heterologous proteins by yeast species and more particularly to an adaptation of the yeast in which the protein is produced.

2. Background and Prior Art

In recent years, yeasts have been widely used as host organisms for the production of heterologous proteins (reviewed by Romanos et al, 1992), including recombinant human albumin (rHA) (Sleep et al, 1990, 1991; Fleer et al, 1991). Yeasts are readily amenable to genetic manipulation, can be grown to high cell density on simple media, and as eukaryotes are suitable for the production of secreted as well as cytosolic proteins.

When yeasts are utilised to produce a desired heterologous protein by secretion into the growth medium, a large number of host-derived proteins may also be present, including other proteins secreted by the host but also intracellular proteins present in the supernatant as the result of leakage from cells or cell lysis. In processes in which the protein is not secreted, there is of course an even higher level of contamination with intracellular yeast proteins. It is necessary to purify the desired protein and to remove these contaminating proteins from the preparation; such methods have been disclosed in WO 92/04367 and EP 524 681. The majority of contaminating proteins will have physicochemical properties sufficiently different from the desired protein to permit efficient separation by standard techniques, such as ion exchange or size exclusion chromatography. The prior art gives the impression that such proteins can be satisfactorily removed by such techniques; see, for example EP 524 681 (Gist-brocades), EP 570 916 (Green Cross) and EP 464 590 (Green Cross). Indeed, we have developed sophisticated chromatographic techniques (unpublished) to remove contaminating proteins from desired proteins.

SUMMARY OF THE INVENTION

We have now also adopted a different approach and have identified the gene responsible for a protein, namely the HSP150 gene, which co-purifies with recombinant human albumin (rHA) and, in principle, with other desired proteins. In accordance with the invention, we eliminate the contaminating protein from the initial fermentation, rather than develop highly sophisticated and complex means of removal during purification. This protein was not previously known to be a co-purifying contaminant.

In one aspect of the invention, the HSP150 gene is functionally deleted from the genome of the host. This has not caused any detrimental effects on production of the desired protein and removes a potential contaminant that has proven difficult to remove by standard purification techniques. Despite the presence of at least two closely related genes encoding proteins very similar to Hsp150, PIR1 and PIR3, in such modified yeast, rHA purified from these organisms does not contain detectable levels of any protein from this family.

The S. cerevisiae Hsp150 protein was originally described by Russo et al (1992) and was shown to be produced constitutively, to be extensively O-glycosylated and to be secreted efficiently into the growth medium. A 7-fold increase in the level of Hsp150 protein was seen when cells grown at 28° C. were shifted to 37° C. Makarow has proposed preparing fusions of Hsp150 (or fragments thereof) and a desired protein, in order to achieve enhanced, controllable secretion (WO 93/18167). The HSP150 gene encodes a primary translation product of 413 amino acids, including an N-terminal secretion signal sequence of 18 amino acids that is not present in the mature protein. A further post-translational processing event occurs C-terminal to a pair of basic residues to yield two subunits of 54 and 341 amino acids which remain associated. The 341 amino acid subunit contains 11 tandem repeats of a 19 amino acid sequence, the function of which is unknown. Homologues of the HSP150 gene were found in *Torulaspora delbrueckii*, *Kluyveromyces marxianus* and *Schizosaccharomyces pombe* (Russo et al, 1992).

The same protein has been designated the PIR2 protein by Toh-e et al (1993). The HSP150/PIR2 gene was shown to be a member of a family of at least three genes (PIR1, PIR2 and PIR3) all of which contain similar internal tandem repeats of approximately 19 amino acids. Homologues of the PIR genes were shown to be present also in *Kluyveromyces lactis* and *Zygosaccharomyces rouxii* (Toh-e et al, 1993). Disruption of the HSP150/PIR2 gene showed that this is not an essential gene (Russo et al, 1992; Toh-e et al, 1993).

In this specification we refer to rHA as the desired protein. However, it is to be understood that the problem addressed by the invention will, in principle, be encountered with any other protein which has similar properties to those of rHA and which is therefore purified in the same way. Thus, the solution provided by the invention, namely elimination of Hsp150, is applicable also to the production of such other proteins.

Our studies have revealed that the Hsp150 protein is inefficiently separated from rHA by ion exchange chromatography. Surprisingly, however, Hsp150 does not appear in the fraction equivalent to the rHA fraction when rHA is absent. For example, when rHA-containing culture supernatant is passed through a cation exchange column under conditions which ensure binding of the rHA to the column (eg pH4.5, conductivity <7 mS), Hsp150 also binds to the column and is eluted under the same conditions as rHA and thus contaminates the rHA preparation. However, when culture supernatant from a yeast that does not secrete rHA is passed through such a column under the same conditions, the Hsp150 protein does not bind to the matrix but passes straight through the column. The eluate fraction does not contain Hsp150 in the absence of rHA. Similarly, the Hsp150 protein does not bind to an anion exchange column run under conditions which would result in binding of albumin (eg pH5.5, 1.5mS) in the absence of rHA, but is present in the rHA eluate fraction when rHA is present. Surprisingly, we have found that the presence of rHA in culture supernatant significantly alters the behaviour of some yeast proteins during chromatographic purification of the rHA such that proteins with physico-chemical properties which indicate that they would be separated from albumin by, for instance, ion exchange chromatography in fact contaminate the rHA preparation and are difficult to remove.

One aspect of the invention provides a process for preparing a desired protein from yeast, comprising culturing the yeast and obtaining the protein, characterised in that the yeast is deficient in heat shock protein 150 (Hsp150).

The most convenient way of achieving this is to create a yeast which has a defect in its genome such that a reduced level of the Hsp150 protein is produced. For example, there may be a deletion, insertion or transposition in the coding sequence or the regulatory regions (or in another gene regulating the expression of the Hsp150 gene) such that little or no Hsp150 protein is produced. Alternatively, the yeast could be transformed to produce an anti-Hsp150 agent, such as an anti-Hsp150 antibody.

To modify the HSP150 gene so that a reduced level of co-purifying protein is produced, site-directed mutagenesis or other known techniques can be employed to create single or multiple mutations, such as replacements, insertions, deletions, and transpositions, as described in Botstein and Shortle, "Strategies and Applications of *In Vitro* Mutagenesis", Science, 229: 193–210 (1985), which is incorporated herein by reference. Suitable mutations include chain termination mutations (clearly stop codons introduced near the 3' end might have insufficient effect on the gene product to be of benefit; the person skilled in the art will readily be able to create a mutation in, say, the 5' three quarters of the coding sequence), point mutations that alter the reading frame, small to large deletions of coding sequence, mutations in the promoter or terminator that affect gene expression and mutations that de-stabilize the mRNA. Some desirable point mutations or specific amino acid substitutions may affect chromatographic behaviour by altering the charge distribution. Hence, the protein produced has a similar primary amino acid sequence to that of native Hsp150, but is functionally distinct such that it will not co-purify with the desired protein. Such a modified protein is not regarded as being Hsp150. Specific mutations can be introduced by an extension of the gene disruption technique known as gene transplacement (Winston, F. et al (1983) *Methods Enrzymol.* 101, 211–228).

Any polypeptides inserted into the Hsp150 protein should not be, and should not create, ligands for the desired protein. Those skilled in the art can readily determine, by simple binding assays, whether a ligand has been used or created. Generally one uses a selectable marker to disrupt a gene sequence, but this need not be the case, particularly if one can detect the disruption event phenotypically. In many instances the insertion of the intervening sequence will be such that a stop codon is present in frame with the Hsp150 sequence and the inserted coding sequence is not translated. Alternatively the inserted sequence may be in a different reading frame to Hsp150.

The gene may have one or more portions (optionally including regulatory regions, up to the whole gene) excised or inverted, or it may have a portion inserted, in order to result either in no production of protein from the HSP150 locus or in the production of protein from the HSP150 locus which does not co-purify with the desired protein.

Preferably, the yeast secretes the desired protein, which is then purified from the fermentation medium. The purification may take place elsewhere; hence, production of culture medium, containing desired protein, in which the level of Hsp150 protein is low or zero is an end in itself.

A protein is generally regarded as co-purifying with Hsp150 if the two are still associated after two dissimilar chromatographic separation techniques (one of which is affinity chromatography for the desired protein) or, if affinity chromatography is not used, if the proteins are still associated after three dissimilar steps (for example an anion exchange, a cation exchange and a gel permeation step). Essentially, the identity of the desired protein is self-defined: if a person skilled in the art finds that his desired protein is, after an otherwise suitable purification process, contaminated with a yeast protein, he can determine (using known methods, which are explained in more detail below) whether that yeast protein is Hsp150 and, if it is, use the yeasts and methods of the invention; if the desired protein is not contaminated with Hsp150, then the need for the present invention will not arise. We have found the process of the invention to be particularly applicable to albumins and to other proteins which have similar physico-chemical properties to albumins, such that they are purified by similar chromatographic techniques. Preferably, the desired protein is a human albumin.

Human serum albumin (HSA) is a protein of 585 amino acids that is present in human serum at a concentration of 35–45 g L$^{-1}$ and represents about 60% of the total serum protein. HSA is responsible for a significant proportion of the osmotic pressure of serum, and also functions as a carrier of endogenous and exogenous ligands. It is used clinically in the treatment of patients with severe burns, shock, or blood loss, and at present is produced commercially by extraction from human blood. The production of recombinant human albumin (rHA) in microorganisms has been disclosed in EP 330 451 and EP 361 991.

The albumin may be a variant of normal HSA/rHA. By "variants" we include insertions, deletions and substitutions, either conservative or non-conservative, where such changes do not substantially alter the oncotic, useful ligand-binding or non-immunogenic properties of albumin. In particular, we include naturally-occurring polymorphic variants of human albumin; fragments of human albumin, for example those fragments disclosed in EP 322 094 (namely HSA (1–n), where n is 369 to 419); and fusions of albumin with other proteins, for example the kind disclosed in WO 90/13653.

By "conservative substitutions" is intended swaps within groups such as Gly, Ala; Val, Ile, Leu; Asp, Glu; Asn, Gln; Ser, Thr; Lys, Arg; and Phe, Tyr.

A second main aspect of the invention provides a yeast transformed to express a desired protein which will co-purify with Hsp150 in chromatographic techniques, characterised in that the yeast is deficient in such Hsp150.

In addition to the transformed host cells themselves, the present invention also contemplates a culture of those cells, preferably a monoclonal (clonally homogeneous) culture, or a culture derived from a monoclonal culture, in a nutrient medium.

The desired protein is produced in conventional ways, for example from a coding sequence inserted in the yeast chromosome or on a free plasmid.

The yeasts are transformed with a coding sequence for the desired protein in any of the usual ways, for example electroporation. Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct can be grown to produce the desired polypeptide. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies.

Useful yeast plasmid vectors include pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413–416 are Yeast Centromere plasmids (YCps).

A variety of methods have been developed to operably link DNA to vectors via complementary cohesive termini. For instance, complementary homopolymer tracts can be added to the DNA segment to be inserted to the vector DNA.

The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or E. coli DNA polymerase I, enzymes that remove protruding, 3'-single-stranded termini with their 3'–5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc. New Haven, Conn., USA.

A desirable way to modify the DNA in accordance with the invention is to use the polymerase chain reaction as disclosed by Saiki et al (1988) Science 239, 487–491. In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

Any yeast which produces an Hsp150 protein can be modified in accordance with the invention. Exemplary genera of yeast contemplated to be useful in the practice of the present invention are Pichia (Hansenula), Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis, and the like.

Preferred genera are those selected from the group consisting of Saccharomyces, Schizosaccharomyces, Kluyveromyces, and Torulaspora. Examples of Saccharomyces spp. are S. cerevisiae, S. italicus and S. rouxii. Examples of Kluyveromyces spp. are K. fragilis, K. lactis and K. marxianus. A suitable Torulaspora species is T. delbrueckii. Examples of Pichia (Hansenula) spp. are P. angusta (formerly H. polymorpha), P. anomala (formerly H. anomala) and P. pastoris.

Homologues of HSP150 have already been shown to be present in a wide range of different yeast genera: Torulaspora sp., Kluyveromyces sp., Schizosaccharomyces sp. and Zygosaccharomyces sp. (Russo et al, 1992; Toh-e et al, 1993). In addition, our own studies have shown by Southern blotting that Pichia sp. possess a homologue of HSP150.

Methods for the transformation of S. cerevisiae are taught generally in EP 251 744, EP 258 067 and WO 90/01063, all of which are incorporated herein by reference.

Suitable promoters for S. cerevisiae include those associated with the PGK1 gene, GAL1 or GAL10 genes, CYC1, PHO5, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, α-mating factor pheromone, a-mating factor pheromone, the PRB1 promoter, the GUT2 promoter, the GPD1 promoter, and hybrid promoters involving hybrids of parts of 5' regulatory regions with parts of 5' regulatory regions of other promoters or with upstream activation sites (eg the promoter of EP-A-258 067).

Convenient regulatable promoters for use in Schizosaccharomyces pombe are the thiamine-repressible promoter from the nmt gene as described by Maundrell (1990) J. Biol. Chem. 265, 10857–10864 and the glucose-repressible fbp1 gene promoter as described by Hoffman & Winston (1990) Genetics 124, 807–816.

Methods of transforming Pichia for expression of foreign genes are taught in, for example, Cregg et al (1993), and various Phillips patents (eg US 4 857 467, incorporated herein by reference), and Pichia expression kits are commercially available from Invitrogen BV, Leek, Netherlands, and Invitrogen Corp., San Diego, Calif. Suitable promoters include AOX1 and AOX2.

The Gellissen et al (1992) paper mentioned above and Gleeson et al (1986) J. Gen. Microbiol. 132, 3459–3465 include information on Hansenula vectors and transformation, suitable promoters being MOX1 and FMD1; whilst EP 361 991, Fleer et al (1991) and other publications from Rhône-Poulenc Rorer teach how to express foreign proteins in Kluyveromyces spp., a suitable promoter being PGK1.

The transcription termination signal is preferably the 3'flanking sequence of a eukaryotic gene which contains proper signals for transcription termination and polyadenylation. Suitable 3'flanking sequences may, for example, be those of the gene naturally linked to the expression control sequence used, ie may correspond to the promoter. Alternatively, they may be different in which case the termination signal of the S. cerevisiae ADH1 gene is preferred.

The desired protein may be initially expressed with a secretion leader sequence, which may be any leader effective in the yeast chosen. Leaders useful in S. cerevisiae include that from the mating factor α polypeptide (MFα-1) and the hybrid leaders of EP-A-387 319. Such leaders (or signals) are cleaved by the yeast before the mature albumin is released into the surrounding medium. Further such leaders include those of S. cerevisiae invertase (SUC2) disclosed in JP 62-096086 (granted as 91/036516), acid phosphatase (PHO5), the pre-sequence of MFα-1, β-glucanase (BGL2) and killer toxin; S. diastaticus glucoamylase II; S. carlsbergensis α-galactosidase (MEL1); K. lactis killer toxin; and Candida glucoamylase.

DESCRIPTION OF THE DRAWINGS

Preferred aspects of the invention will now be described in more detail, with reference to the accompanying drawings, in which.

DETAILED DESCRIPTION OF THE INVENTION

All standard recombinant DNA procedures are as described in Sambrook et al (1989) unless otherwise stated.

The DNA sequences encoding rHA are derived from the cDNA disclosed in EP 201 239.

Example 1

The HSP150 gene was mutated by the process of gene disruption (Rothstein, 1983) which effectively deleted part of the HSP150 coding sequence, thereby preventing the production of Hsp150.

Four oligonucleotides suitable for the PCR amplification of the 5' and 3' ends of the HSP150 gene (Russo et al, 1992) were synthesized using an Applied Biosystems 380B Oligonucleotide Synthesizer.

5' End
LRE45: 5'-CTATTTCCTATTTCGGGAATTCTTAAAGA-CAAAAAGCTC-3' (SEQ ID NO: 1)
LRE46: 5'-GGCTGTGGTGCTGCAGATGATGCGCTGG-3' (SEQ ID NO: 2)
3' End
LRE47: 5'-GCTACTTCCGCTTCTGCAGCCGCTACCT-CC-3' (SEQ ID NO: 3)
LRE48: 5'-GCCGTGTAGCGAGGGAATTCTGTGGTCA-CGATCACTCG-3' (SEQ ID NO: 4)

Note, LRE45 and LRE48 contain changes in the HSP150 gene sequence so as to introduce EcoRI sites into the 5' or the 3' end of the HSP150 gene PCR products. LRE46 and LRE47 both contain Pst I sites naturally present in the HSP150 gene sequence (SEQ 1).

PCR was carried out to amplify individually the 5' and 3' ends of the HSP150 gene, using LRE45 and LRE46 or LRE47 and LRE48 respectively, from the DNA from S. cerevisiae genomic DNA (Clontech Laboratories, Inc.).

Figure 1:
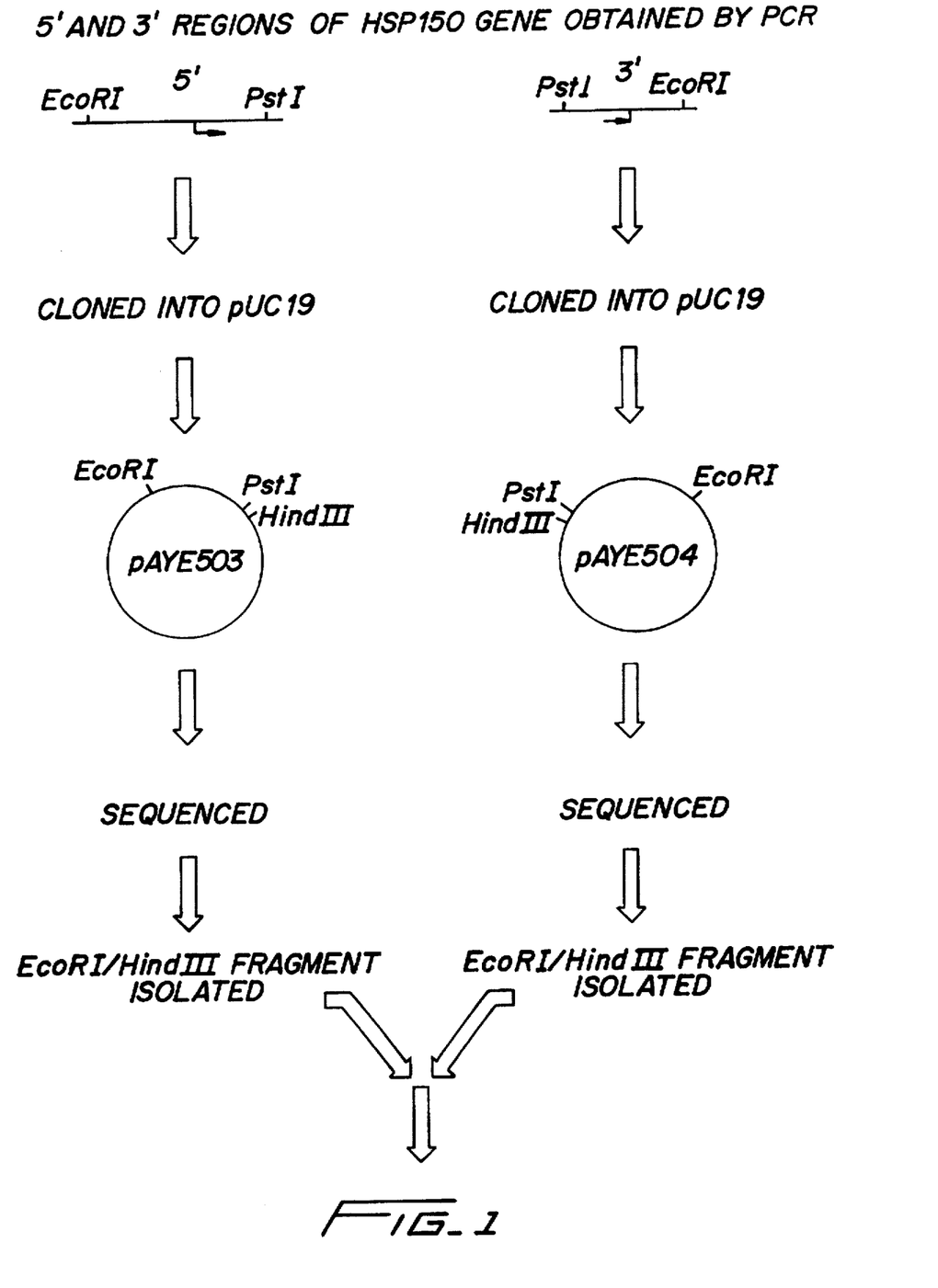
FIG. 1 is a scheme showing the preparation of an EcoRI HSP150-URA3-HSP150 fragment used to transform a yeast strain (DBU3) and disrupt the HSP150 gene (Example 1)

Conditions were as follows: 1 µg/ml genomic DNA, ≅ 1.2×10$^{-10}$ moles of each primer, denature at 94° C. for 61 seconds, anneal at 37° C. for 121 seconds, DNA synthesis at 72° C. for 181 seconds for 30 cycles, with a 10 second extension to the DNA synthesis step after each cycle, followed by a 4° C. soak. PCR was carried out using a Perkin-Elmer-Cetus Thermal cycler and a Perkin-Elmer-Cetus PCR kit was used according to the manufacturer's recommendations. PCR products were analysed by gel electrophoresis and were found to be of the expected size. Each PCR product was digested with EcoRI and PstI and cloned into EcoRI/PstI digested pUC19 (Yanisch-Perron et al, 1985) to form pAYE503 (containing the 5' end of the HSP150 gene) and pAYE504 (containing the 3' end of the HSP150 gene) (see FIG. 1).

Plasmid DNA sequencing was carried out on pAYE503 and pAYE504 to confirm that the inserts were the desired sequences. pAYE503 and pAYE504 were digested with EcoRI and HindIII and the HSP150 gene fragments were isolated and cloned together into pUC19XH (a derivative of pUC19 lacking a HindIII site in its polylinker) to form pAYE505. The URA3 gene was isolated from YEp24 (Botstein et al, 1979) as a HindIII fragment and cloned into the HindIII site of pAYE505 to form pAYE506 (FIG. 1). pAYE506 contains a selectable marker (URA3) flanked by 5' and 3' regions of the HSP150 gene.

To construct a strain lacking the capacity to produce HSP150, a ura3 derivative of DB1 cir° pAYE316 (Sleep et al, 1991) was obtained by random chemical mutagenesis and selection for resistance to 5-fluoro-orotic acid (Boeke et al, 1987). Plasmid pAYE316 is based on the 2 µm plasmid and contains a coding sequence for human albumin under the control of the yeast PRB1 promoter, with an ADH1 terminator and a LEU2 selectable marker.

The strain was grown overnight in 100 mL buffered minimal medium (Yeast Nitrogen Base [without amino acids, without ammonium sulphate, Difco], (NH$_4$)$_2$SO$_4$ 5 g/L, citric acid monohydrate 6.09 g/L, NaHPO$_4$ 20.16 g/L, sucrose 20 g/L, pH6.5) and the cells were collected by centrifugation and then washed once with sterile water. The cells were then resuspended in 10 mL sterile water and 2 mL aliquots were placed in separate 15 mL Falcon tubes. A 5 mg/mL solution of N-methyl-N'-nitro-N-nitrosoguanidine (NTG) was then added to the tubes as follows: 0µL, 20µL, 40µL, 80µL or 160µL. The cells were then incubated at 30° C. for 20 min and then centrifuged and washed three times with sterile water. Finally, the cells were resuspended in 1 mL YEP (1%w/v yeast extract, 2%w/v, Bacto peptone) and stored at 4° C. The percentage of cells that survived the mutagenic treatment was determined by spreading dilutions of the samples on YEP plates containing 2%w/v sucrose and incubating at 30° C. for 3 days. Cells from the treatment which gave approximately 50% survival were grown on YEP plates containing 2%w/v sucrose and then replica-plated onto YNB minimal medium containing 2%w/v sucrose and supplemented with 5-fluoro-orotic acid (1 mg/mL) and uracil (50µg/mL). Colonies able to grow on this medium were purified, tested to verify that they were unable to grow in the absence of uracil supplementation and that this defect could be corrected by introduction of the URA3 gene by transformation.

The ura3 strain, DBU3 cir° (pAYE316), was transformed with EcoRI digested pAYE506 and Ura+ transformants were selected. The disruption of the HSP150 gene in these transformants was confirmed by Southern blot analysis using a fragment comprising the 5' and 3' ends of the HSP150 gene (the EcoRI fragment from pAYE505) as a probe.

The yeast was then grown to high cell density by fed batch culture in minimal medium in a fermenter (Collins, 1990). Briefly, a fermenter of 10 L working volume was filled to 5 L with an initial batch medium containing 50 mL/L of a concentrated salts mixture (Table 1), 10 mL/L of a trace elements solution (Table 2), 50 mL/L of a vitamins mixture (Table 3) and 20 g/L sucrose. An equal volume of feed medium containing 100 mL/L of the salts mixture, 20 mL/L of the trace elements mixture, 100 mL/L of vitamins solution and 500 g/L sucrose was held in a separate reservoir connected to the fermenter by a metering pump. The pH was maintained at 5.7 ±0.2 by the automatic addition of ammonium hydroxide or sulphuric acid, and the temperature was maintained at 30° C. The stirrer speed was adjusted to give a dissolved oxygen tension of > 20% air saturation at 1 v/v/min air flow rate.

TABLE 1

| Salts Mixture | |
| --- | --- |
| Chemical | Concentration (g/L) |
| KH$_2$PO$_4$ | 114.0 |
| MgSO$_4$ | 12.0 |
| CaCl$_2$.6H$_2$O | 3.0 |
| Na$_2$EDTA | 2.0 |

TABLE 2

| Trace Elements Solution | |
| --- | --- |
| Chemical | Concentration (g/L) |
| ZnSO$_4$.7H$_2$O | 3.0 |
| FeSO$_4$.7H$_2$O | 10.0 |
| MnSO$_4$.4H$_2$O | 3.2 |
| CuSO$_4$.5H$_2$O | 0.079 |

TABLE 2-continued

Trace Elements Solution

| Chemical | Concentration (g/L) |
|---|---|
| $H_3BO_3$ | 1.5 |
| KI | 0.2 |
| $Na_2MoO_4.2H_2O$ | 0.5 |
| $CoCl_2.6H_2O$ | 0.56 |
| $H_3PO_4$ | 75mL/L |

TABLE 3

Vitamins Solution

| Chemical | Concentration (g/L) |
|---|---|
| Ca pantothenate | 1.6 |
| Nicotinic acid | 1.2 |
| m-inositol | 12.8 |
| Thiamine HCl | 0.32 |
| Pyridoxine HCl | 0.8 |
| Biotin | 0.008 |

The fermenter was inoculated with 100 mL of an overnight culture of *S. cerevisiae* grown in buffered minimal medium (Yeast nitrogen base [without amino acids, without ammonium sulphate, Difco] 1.7 g/L, $(NH_4)_2SO_4$ 5 g/L, citric acid monohydrate 6.09 g/L, $Na_2HPO_4$ 20.16 g/L, sucrose 20 g/L, pH6.5). The initial batch fermentation proceeded until the carbon source had been consumed, at which point the metering pump was switched on and the addition of feed was computer controlled (the micro MFCS system, B. Braun, Melsungen, Germany) using an algorithm based on that developed by Wang et al (1979). A mass spectrometer was used in conjunction with the computer control system to monitor the off gases from the fermentation and to control the addition of feed to maintain a set growth rate (eg $0.1^{-1}$). Maximum conversion of carbon substrate into biomass is achieved by maintaining the respiratory coefficient below 1.2 (Collins, 1990) and, by this means, cell densities of approximately 100 g/L cell dry weight can be achieved.

The fermentation broth was centrifuged to remove the cells and then subjected to affinity chromatographic purification as follows. The culture supernatant was passed through a Cibacron Blue F3GA Sepharose column (Pharmacia) which was then washed with 0.1 M phosphate glycine buffer, pH8.0. The rHA was then eluted from the column with 2 M NaCl, 0.1 M phosphate glycine, pH8.0. The albumin may alternatively be purified from the culture medium by any of the variety of known techniques for purifying albumin from serum or fermentation culture medium, for example those disclosed in WO 92/04367, Maurel et al (1989), Curling (1980) and EP 524 681.

Analysis of rHA purified from Hsp150 strains revealed that no HSP150 protein was present in these samples. HSP150 protein is determined using prior art techniques such as ELISA or Western blotting.

Anti-HSP150 antibodies are disclosed in Russo et al (1992) *Proc. Nat. Acad. Sci.* (USA) 89, 3671–3675.

Example 2

The HSP150 protein coding sequence was deleted by using alternative fragments of the cloned HSP150 sequences as follows.

Figure 2:
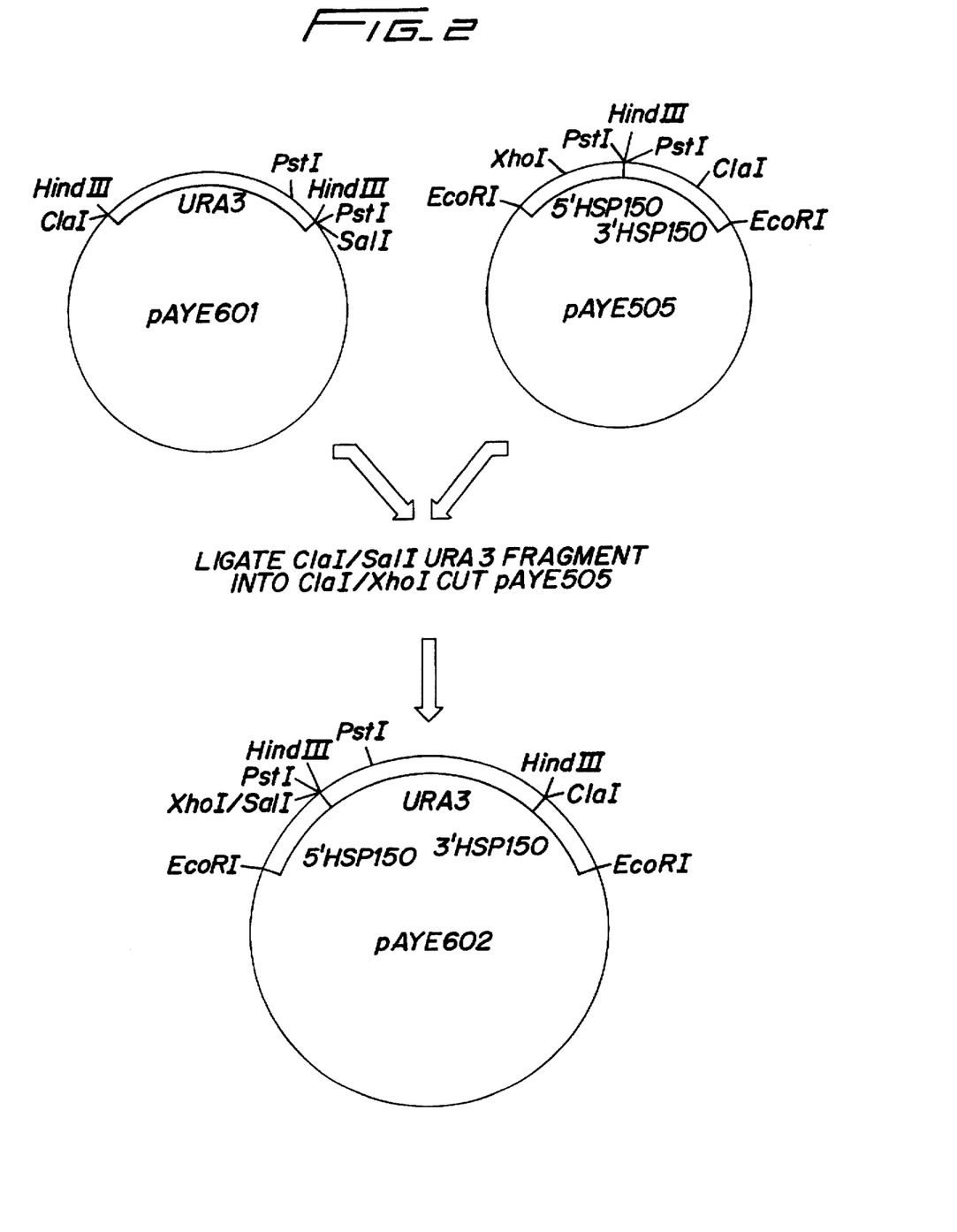
FIG. 2 is a scheme showing the preparation of a further EcoRI fragment used to remove the HSP150 coding sequence altogether (Example 2).

The URA3 HindIII fragment from YEp24 (see Example 1) was cloned into pIC19R (Marsh J. L. et al (1984) *Gene* 32, 481–485) at HindIII to form pAYE601 and then excised as a SalI/ClaI fragment and inserted into pAYE505 at the XhoI and ClaI sites to form pAYE602 (FIG. 2). This plasmid was digested with EcoRI and then used to transform DBU3 cir° (pAYE316), selecting for Ura+ transformants. The disruption of the HSP150 gene in these transformants was confirmed by Southern blot analysis as described in Example 1.

Thus, in this example, the whole of the HSP150 coding sequence is removed, whereas in Example 1 the sequence is disrupted to yield non-functional protein.

Example 3

Southern blotting has revealed an Hsp150 homologue in *Hansenula polymorpha* (now called *Pichia angusta*). The *P. angusta* gene may be functionally deleted by ways analogous to those in Examples 1 and 2.

References

Boeke, J. D. et al (1987) *Methods Enzymol*. 154, 164–175.

Botstein, D. et al (1979) *Gene* 8, 17–24.

Collins, S. H. (1990) In Protein Production by Biotechnology (Harris, T. J. R., ed.) pp 61–77, Elsevier, Barking, Essex.

Curling (1980) "Albumin Purification by Ion Exchange Chromatography", in "Methods of Plasma Protein Purification", Ed. Curling, J. M., Academic Press, London.

Fleer, R. et al (1991) *Bio/Technology* 9, 968–975.

Maurel et al (1989) "Biotechnology of Plasma Proteins", Colloque INSERM 175, 19–24.

Romanos, M. et al (1992) *Yeast* 8, 423–488.

Rothstein, R. J. (1983) *Methods Enzymol*. 101, 202–211.

Russo, P. et al (1992) *Proc. Natl. Acad. Sci. USA* 89, 3671–3675.

Sambrook, J. et al (1989) *Molecular Cloning: a Laboratory Manual*, 2nd edition. Cold Spring Harbor Laboratory Press, Cold Spring Harbor, N.Y.

Sleep, D. et al (1991) *Bio/Technology* 9, 183–187.

Toh-e et al (1993) *Yeast* 9, 481–494.

Wang, H. Y. et al (1979) *Biotechnology & Bioeng*. 21, 975.

Yanisch-Perron, C. et al (1985) *Gene* 33, 103–119.

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
( A ) LENGTH: 40 base pairs (B) TYPE: nucleic acid
                    (C) STRANDEDNESS: single
                    (D) TOPOLOGY: linear (ii) MOLECULE TYPE: cDNA (iii) HYPOTHETICAL: NO (ix) FEATURE:
                    (A) NAME/KEY: misc_feature
                    (B) LOCATION: 1..40
                    (D) OTHER INFORMATION: /note= "Oligonucleotide for PCR
                        amplification of 5'end of Hsp150 gene."

(xi) SEQUENCE DESCRIPTION: SEQ ID NO: 1:

CTATTTCCTA TTTCGGGAAT TCTTAAAGAC AAAAAAGCTC           40

(2) INFORMATION FOR SEQ ID NO: 2:

(i) SEQUENCE CHARACTERISTICS:
                    (A) LENGTH: 28 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (ix) FEATURE:
                    (A) NAME/KEY: misc_feature
                    (B) LOCATION: 1..28
                    (D) OTHER INFORMATION: /note= "Oligonucleotide for PCR
                        amplification of the 5'end of the Hsp150 gene."

(xi) SEQUENCE DESCRIPTION: SEQ ID NO: 2:

GGCTGTGGTG CTGCAGATGA TGCGCTGG                        28

(2) INFORMATION FOR SEQ ID NO: 3:

(i) SEQUENCE CHARACTERISTICS:
                    (A) LENGTH: 30 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (ix) FEATURE:
                    (A) NAME/KEY: misc_feature
                    (B) LOCATION: 1..30
                    (D) OTHER INFORMATION: /note= "Oligonucleotide for PCR
                        amplification of 3'end of the Hsp150 gene."

(xi) SEQUENCE DESCRIPTION: SEQ ID NO: 3:

GCTACTTCCG CTTCTGCAGC CGCTACCTCC                      30

(2) INFORMATION FOR SEQ ID NO: 4:

(i) SEQUENCE CHARACTERISTICS:
                    (A) LENGTH: 38 base pairs
                    (B) TYPE: nucleic acid
                    (C) STRANDEDNESS: single
                    (D) TOPOLOGY: linear (ii) MOLECULE TYPE: cDNA (iii) HYPOTHETICAL: NO (ix) FEATURE:
                    (A) NAME/KEY: misc_feature
                    (B) LOCATION: 1..38

( D ) OTHER INFORMATION: /note= "Oligonucleotide for PCR
amplification of the 3'end of the Hsp150 gene."

( x i ) SEQUENCE DESCRIPTION: SEQ ID NO: 4:

GCCGTGTAGC GAGGGAATTC TGTGGTCACG ATCACTCG                                38

( 2 ) INFORMATION FOR SEQ ID NO: 5:

( i ) SEQUENCE CHARACTERISTICS:
       ( A ) LENGTH: 2048 base pairs
       ( B ) TYPE: nucleic acid
       ( C ) STRANDEDNESS: single
       ( D ) TOPOLOGY: linear ( i i ) MOLECULE TYPE: DNA (genomic)

( i i i ) HYPOTHETICAL: NO ( v i ) ORIGINAL SOURCE:
       ( A ) ORGANISM: Saccharomyces cerevisiae ( i x ) FEATURE:
       ( A ) NAME/KEY: CDS
       ( B ) LOCATION: 397..1638

( x i ) SEQUENCE DESCRIPTION: SEQ ID NO: 5:

| | | | | | |
|---|---|---|---|---|---|
| AGTGATCTTA | CTATTTCCTA | TTTCGGAAAT | TATTAAAGAC | AAAAAAGCTC | ATTAATGGCT | 60 |
| TTCCGTCTGT | AGTGATAAGT | CGCCAACTCA | GCCTAATTTT | TCATTTCTTT | ACCAGATCAG | 120 |
| GAAAACTAAT | AGTACAAATG | AGTGTTTTCT | CAAGCGGAAC | ACCACATTTT | GAGCTAAATT | 180 |
| TAGATTTTGG | TCAAAATAAG | AAAGATCCTA | AAAAAGGAAT | GGTTGGTGAA | AAATTTATTA | 240 |
| GCTTGAATGG | TAGGAATCCT | CGAGATATAA | AAGGAACACT | TGAAGTCTAA | CGACAATCAA | 300 |
| TTTCGATTAT | GTCCTTCCTT | TTACCTCAAA | GCTCAAAAAA | ATATCAATAA | GAAACTCATA | 360 |
| TTCCTTTTCT | AACCCTAGTA | CAATAATAAT | AATATA ATG | CAA TAC AAA | AAG ACT | 414 |
| | | | | Met Gln Tyr Lys | Lys Thr | |
| | | | | 1 | 5 | |

| TTG | GTT | GCC | TCT | GCT | TTG | GCC | GCT | ACT | ACA | TTG | GCC | GCC | TAT | GCT | CCA | 462 |
|---|---|---|---|---|---|---|---|---|---|---|---|---|---|---|---|---|
| Leu | Val | Ala | Ser | Ala | Leu | Ala | Ala | Thr | Thr | Leu | Ala | Ala | Tyr | Ala | Pro | |
| | | | 10 | | | | | 15 | | | | | 20 | | | |

| TCT | GAG | CCT | TGG | TCC | ACT | TTG | ACT | CCA | ACA | GCC | ACT | TAC | AGC | GGT | GGT | 510 |
|---|---|---|---|---|---|---|---|---|---|---|---|---|---|---|---|---|
| Ser | Glu | Pro | Trp | Ser | Thr | Leu | Thr | Pro | Thr | Ala | Thr | Tyr | Ser | Gly | Gly | |
| | | 25 | | | | | 30 | | | | | 35 | | | | |

| GTT | ACC | GAC | TAC | GCT | TCC | ACC | TTC | GGT | ATT | GCC | GTT | CAA | CCA | ATC | TCC | 558 |
|---|---|---|---|---|---|---|---|---|---|---|---|---|---|---|---|---|
| Val | Thr | Asp | Tyr | Ala | Ser | Thr | Phe | Gly | Ile | Ala | Val | Gln | Pro | Ile | Ser | |
| | 40 | | | | | 45 | | | | | 50 | | | | | |

| ACT | ACA | TCC | AGC | GCA | TCA | TCT | GCA | GCC | ACC | ACA | GCC | TCA | TCT | AAG | GCC | 606 |
|---|---|---|---|---|---|---|---|---|---|---|---|---|---|---|---|---|
| Thr | Thr | Ser | Ser | Ala | Ser | Ser | Ala | Ala | Thr | Thr | Ala | Ser | Ser | Lys | Ala | |
| 55 | | | | | 60 | | | | | 65 | | | | | 70 | |

| AAG | AGA | GCT | GCT | TCC | CAA | ATT | GGT | GAT | GGT | CAA | GTC | CAA | GCT | GCT | ACC | 654 |
|---|---|---|---|---|---|---|---|---|---|---|---|---|---|---|---|---|
| Lys | Arg | Ala | Ala | Ser | Gln | Ile | Gly | Asp | Gly | Gln | Val | Gln | Ala | Ala | Thr | |
| | | | | 75 | | | | | 80 | | | | | 85 | | |

| ACT | ACT | GCT | TCT | GTC | TCT | ACC | AAG | AGT | ACC | GCT | GCC | GCC | GTT | TCT | CAG | 702 |
|---|---|---|---|---|---|---|---|---|---|---|---|---|---|---|---|---|
| Thr | Thr | Ala | Ser | Val | Ser | Thr | Lys | Ser | Thr | Ala | Ala | Ala | Val | Ser | Gln | |
| | | | | 90 | | | | | 95 | | | | | 100 | | |

| ATC | GGT | GAT | GGT | CAA | ATC | CAA | GCT | ACT | ACT | AAG | ACT | ACC | GCT | GCT | GCT | 750 |
|---|---|---|---|---|---|---|---|---|---|---|---|---|---|---|---|---|
| Ile | Gly | Asp | Gly | Gln | Ile | Gln | Ala | Thr | Thr | Lys | Thr | Thr | Ala | Ala | Ala | |
| | | | 105 | | | | | 110 | | | | | 115 | | | |

| GTC | TCT | CAA | ATT | GGT | GAT | GGT | CAA | ATT | CAA | GCT | ACC | ACC | AAG | ACT | ACC | 798 |
|---|---|---|---|---|---|---|---|---|---|---|---|---|---|---|---|---|
| Val | Ser | Gln | Ile | Gly | Asp | Gly | Gln | Ile | Gln | Ala | Thr | Thr | Lys | Thr | Thr | |
| | | 120 | | | | | 125 | | | | | 130 | | | | |

| TCT | GCT | AAG | ACT | ACC | GCC | GCT | GCC | GTT | TCT | CAA | ATC | AGT | GAT | GGT | CAA | 846 |
|---|---|---|---|---|---|---|---|---|---|---|---|---|---|---|---|---|
| Ser | Ala | Lys | Thr | Thr | Ala | Ala | Ala | Val | Ser | Gln | Ile | Ser | Asp | Gly | Gln | |
| 135 | | | | | 140 | | | | | 145 | | | | | 150 | |

```
ATC CAA GCT ACC ACC ACT ACT TTA GCC CCA AAG AGC ACC GCT GCT GCC    894
Ile Gln Ala Thr Thr Thr Thr Leu Ala Pro Lys Ser Thr Ala Ala Ala
            155                 160                 165

GTT TCT CAA ATC GGT GAT GGT CAA GTT CAA GCT ACC ACC ACT ACT TTA    942
Val Ser Gln Ile Gly Asp Gly Gln Val Gln Ala Thr Thr Thr Thr Leu
                170                 175                 180

GCC CCA AAG AGC ACC GCT GCT GCC GTT TCT CAA ATC GGT GAT GGT CAA    990
Ala Pro Lys Ser Thr Ala Ala Ala Val Ser Gln Ile Gly Asp Gly Gln
            185                 190                 195

GTT CAA GCT ACT ACT AAG ACT ACC GCT GCT GCT GTC TTT CAA ATT GGT   1038
Val Gln Ala Thr Thr Lys Thr Thr Ala Ala Ala Val Phe Gln Ile Gly
        200                 205                 210

GAT GGT CAA GTT CTT GCT ACC ACC AAG ACT ACT CGT GCC GCC GTT TCT   1086
Asp Gly Gln Val Leu Ala Thr Thr Lys Thr Thr Arg Ala Ala Val Ser
215                 220                 225                 230

CAA ATC GGT GAT GGT CAA GTT CAA GCT ACT ACC AAG ACT ACC GCT GCT   1134
Gln Ile Gly Asp Gly Gln Val Gln Ala Thr Thr Lys Thr Thr Ala Ala
                235                 240                 245

GCT GTC TCT CAA ATC GGT GAT GGT CAA GTT CAA GCA ACT ACC AAA ACC   1182
Ala Val Ser Gln Ile Gly Asp Gly Gln Val Gln Ala Thr Thr Lys Thr
            250                 255                 260

ACT GCC GCA GCT GTT TCC CAA ATT ACT GAC GGT CAA GTT CAA GCC ACT   1230
Thr Ala Ala Ala Val Ser Gln Ile Thr Asp Gly Gln Val Gln Ala Thr
            265                 270                 275

ACA AAA ACC ACT CAA GCA GCC AGC CAA GTA AGC GAT GGC CAA GTC CAA   1278
Thr Lys Thr Thr Gln Ala Ala Ser Gln Val Ser Asp Gly Gln Val Gln
        280                 285                 290

GCT ACT ACT GCT ACT TCC GCT TCT GCA GCC GCT ACC TCC ACT GAC CCA   1326
Ala Thr Thr Ala Thr Ser Ala Ser Ala Ala Ala Thr Ser Thr Asp Pro
295                 300                 305                 310

GTC GAT GCT GTC TCC TGT AAG ACT TCT GGT ACC TTA GAA ATG AAC TTA   1374
Val Asp Ala Val Ser Cys Lys Thr Ser Gly Thr Leu Glu Met Asn Leu
                315                 320                 325

AAG GGC GGT ATC TTA ACT GAC GGT AAG GGT AGA ATT GGT TCT ATT GTT   1422
Lys Gly Gly Ile Leu Thr Asp Gly Lys Gly Arg Ile Gly Ser Ile Val
            330                 335                 340

GCT AAC AGA CAA TTC CAA TTT GAC GGT CCA CCA CCA CAA GCT GGT GCC   1470
Ala Asn Arg Gln Phe Gln Phe Asp Gly Pro Pro Pro Gln Ala Gly Ala
            345                 350                 355

ATC TAC GCT GCT GGT TGG TCT ATA ACT CCA GAC GGT AAC TTG GCT ATT   1518
Ile Tyr Ala Ala Gly Trp Ser Ile Thr Pro Asp Gly Asn Leu Ala Ile
        360                 365                 370

GGT GAC AAT GAT GTC TTC TAC CAA TGT TTG TCC GGT ACT TTC TAC AAC   1566
Gly Asp Asn Asp Val Phe Tyr Gln Cys Leu Ser Gly Thr Phe Tyr Asn
375                 380                 385                 390

TTG TAC GAC GAA CAC ATT GGT AGT CAA TGT ACT CCA GTC CAC TTG GAA   1614
Leu Tyr Asp Glu His Ile Gly Ser Gln Cys Thr Pro Val His Leu Glu
                395                 400                 405

GCT ATC GAT TTG ATA GAC TGT TAAGCAGAAA ACTATTAGTT CTTTTATCCT       1665
Ala Ile Asp Leu Ile Asp Cys
            410

ATGACTTTT TCTCATTTGC ATTGATTAGA AAGGAAAAAA AGAAGTGTCC TTTTCTACTA   1725

TACTCTAGT CGCATCCATT CCTTTGCATT TATCTTTTCT GCGGTTGGCC AATCCATTCT   1785

CCGAGAATT TGGCTAGCCA TACTTGATGT TTTCCCATTA TTGGTTCGTT TGGCAATGCT   1845

ATTTTCTTA ATTGCCCCTT ATATACTCTT CCATAAAATG TTTTTTTTAT AACTAATTTT   1905

TGTATATCA TTATCTAATA ATCTTATAAA ATGTTAAAAA GACTTGGAAA GCAACGAGTG   1965

TCGTGACCA CATAATTGCC TCGCTACACG GCAAAAATAA GCCAGTCCTA ATGTGTATAT   2025
```

AAAGGCTGC ATGTGGCTAC GTC                                                                    2048

( 2 ) INFORMATION FOR SEQ ID NO: 6:

( i ) SEQUENCE CHARACTERISTICS:
      ( A ) LENGTH: 413 amino acids
      ( B ) TYPE: amino acid
      ( D ) TOPOLOGY: linear    ( i i ) MOLECULE TYPE: protein    ( x i ) SEQUENCE DESCRIPTION: SEQ ID NO: 6:

```
Met Gln Tyr Lys Lys Thr Leu Val Ala Ser Ala Leu Ala Ala Thr
 1               5                  10                  15

Leu Ala Ala Tyr Ala Pro Ser Glu Pro Trp Ser Thr Leu Thr Pro Thr
            20                  25                  30

Ala Thr Tyr Ser Gly Gly Val Thr Asp Tyr Ala Ser Thr Phe Gly Ile
        35                  40                  45

Ala Val Gln Pro Ile Ser Thr Thr Ser Ser Ala Ser Ser Ala Ala Thr
    50                  55                  60

Thr Ala Ser Ser Lys Ala Lys Arg Ala Ala Ser Gln Ile Gly Asp Gly
65                  70                  75                  80

Gln Val Gln Ala Ala Thr Thr Thr Ala Ser Val Ser Thr Lys Ser Thr
                    85                  90                  95

Ala Ala Ala Val Ser Gln Ile Gly Asp Gly Gln Ile Gln Ala Thr Thr
            100                 105                 110

Lys Thr Thr Ala Ala Ala Val Ser Gln Ile Gly Asp Gly Gln Ile Gln
        115                 120                 125

Ala Thr Thr Lys Thr Thr Ser Ala Lys Thr Thr Ala Ala Ala Val Ser
    130                 135                 140

Gln Ile Ser Asp Gly Gln Ile Gln Ala Thr Thr Thr Leu Ala Pro
145                 150                 155                 160

Lys Ser Thr Ala Ala Ala Val Ser Gln Ile Gly Asp Gly Gln Val Gln
                    165                 170                 175

Ala Thr Thr Thr Thr Leu Ala Pro Lys Ser Thr Ala Ala Ala Val Ser
            180                 185                 190

Gln Ile Gly Asp Gly Gln Val Gln Ala Thr Thr Lys Thr Thr Ala Ala
        195                 200                 205

Ala Val Phe Gln Ile Gly Asp Gly Gln Val Leu Ala Thr Thr Lys Thr
    210                 215                 220

Thr Arg Ala Ala Val Ser Gln Ile Gly Asp Gly Gln Val Gln Ala Thr
225                 230                 235                 240

Thr Lys Thr Thr Ala Ala Ala Val Ser Gln Ile Gly Asp Gly Gln Val
                    245                 250                 255

Gln Ala Thr Thr Lys Thr Thr Ala Ala Ala Val Ser Gln Ile Thr Asp
            260                 265                 270

Gly Gln Val Gln Ala Thr Thr Lys Thr Thr Gln Ala Ala Ser Gln Val
        275                 280                 285

Ser Asp Gly Gln Val Gln Ala Thr Thr Ala Thr Ser Ala Ser Ala Ala
    290                 295                 300

Ala Thr Ser Thr Asp Pro Val Asp Ala Val Ser Cys Lys Thr Ser Gly
305                 310                 315                 320

Thr Leu Glu Met Asn Leu Lys Gly Gly Ile Leu Thr Asp Gly Lys Gly
                    325                 330                 335

Arg Ile Gly Ser Ile Val Ala Asn Arg Gln Phe Gln Phe Asp Gly Pro
            340                 345                 350
```

| | | | | | | | | | | | | | | | |
|---|---|---|---|---|---|---|---|---|---|---|---|---|---|---|---|
| Pro | Pro | Gln<br>355 | Ala | Gly | Ala | Ile | Tyr<br>360 | Ala | Ala | Gly | Trp | Ser<br>365 | Ile | Thr | Pro |
| Asp | Gly<br>370 | Asn | Leu | Ala | Ile | Gly<br>375 | Asp | Asn | Asp | Val | Phe<br>380 | Tyr | Gln | Cys | Leu |
| Ser<br>385 | Gly | Thr | Phe | Tyr | Asn<br>390 | Leu | Tyr | Asp | Glu | His<br>395 | Ile | Gly | Ser | Gln | Cys<br>400 |
| Thr | Pro | Val | His | Leu<br>405 | Glu | Ala | Ile | Asp | Leu<br>410 | Ile | Asp | Cys | | | |

We claim:

1. A process for preparing a desired protein from a heat shock protein 150 (Hsp150)-deficient yeast comprising: culturing the Hsp150-deficient yeast, obtaining said desired protein from said cultured Hsp150-deficient yeast, wherein said desired protein is not Hsp150 or an Hsp150 fusion protein.

2. The process of claim 1, wherein said Hsp150- deficient yeast has a defect in its genome such that a reduced level of Hsp150 protein is produced.

3. The process of claim 1, wherein said yeast is recombinant yeast and said desired protein is albumin.

4. The process of claim 1, wherein said yeast is recombinant yeast and said desired protein is human albumin.

5. The process of claim 1, wherein said Hsp150-deficient yeast is selected from the group consisting of: Torulaspora, Kluyveromyces, Schizosaccharomyces, Pichia and Saccharomyces.

6. The process of claim 1, wherein said desired protein is secreted from said Hsp150-deficient yeast into the medium surrounding said Hsp150-deficient yeast, and purified therefrom.

7. A purified recombinant protein that co-purifies with Hsp150 product prepared by the process of claim 1, said protein product containing no Hsp150 protein.

8. The process of claim 2, wherein said Hsp150-deficient yeast produces substantially less Hsp150 than wild-type yeast of the same genus and species.

9. The process of claim 5, wherein said Hsp150-deficient yeast is S. cerevisiae.

10. A culture medium containing desired protein prepared by the process of claim 6.

11. A process for preparing a desired protein from a yeast genetically incapable of producing Hsp150 protein comprising: culturing said yeast, obtaining said desired protein from said cultured yeast, wherein said desired protein is not Hsp150 or an Hsp150 fusion protein.

12. The process of claim 11, wherein said yeast has a defect in its genome such that it is incapable of producing Hsp150 protein.

13. The process of claim 11, wherein said yeast is recombinant yeast and said desired protein is albumin.

14. The process of claim 11, wherein said yeast is recombinant yeast and said desired protein is human albumin.

15. The process of claim 11, wherein said yeast is selected from the group consisting of: Torulaspora, Kluyveromyces, Schizosaccharomyces, Pichia and Saccharomyces.

16. The process of claim 11, wherein said desired protein is secreted from said Hsp150-deficient yeast into the medium surrounding said Hsp150-deficient yeast, and purified therefrom.

17. A purified recombinant protein product that co-purifies with Hsp150 prepared by the process of claim 11, said protein product containing no Hsp150 protein.

18. The process of claim 12, wherein said Hsp150-deficient yeast produces substantially less heat shock protein 150 (Hsp150 ) than wild-type yeast of the same genus and species.

19. The process of claim 15, wherein said yeast is S. cerevisiae.

20. A culture medium containing the desired protein prepared by the process of claim 16.

21. A yeast deficient in Hsp150 transformed to express a desired protein which will co-purify with Hsp150 in chromatographic techniques, wherein said desired protein is not an Hsp150 fusion protein.

22. The yeast of claim 21, wherein said yeast has an alteration in its genome that prevents production of Hsp150 protein.

23. The yeast of claim 21, wherein said desired protein is albumin.

24. The yeast of claim 21, wherein said desired protein is human albumin.

25. The yeast of claim 21 selected from the group consisting of: Torulaspora, Kluyveromyces, Schizosaccharomyces, Pichia and Saccharomyces.

26. The yeast of claim 21, wherein said yeast is transformed with a DNA construct such that the desired protein is secreted from yeast into the medium surrounding said yeast during the culturing thereof.

27. The yeast of claim 22, wherein said alteration in said genome is the result of site-directed mutagenesis.

28. The yeast of claim 25, wherein said yeast is S. cerevisiae.

29. A method for preparing a Hsp-150 deficient yeast transformed to express a desired protein which will co-purify with Hsp150 comprising:
   (i) transforming the yeast with a coding sequence for expression of the desired protein;
   (ii) disrupting the genome of the yeast such that the yeast is prevented from producing Hsp150,
   wherein steps (i) or (ii) may be carried out in either order or simultaneously.

* * * * *